United States Patent [19]

McCoy et al.

[11] Patent Number: 5,338,675

[45] Date of Patent: Aug. 16, 1994

[54] TOXIC METABOLIC PRODUCT OF HIRSUTELLA SP.

[75] Inventors: Clayton W. McCoy, Winter Park, Fla.; Alain J. Vey, Saint-Christol; Isabelle M. Mazet, Cheval Blanc, both of France

[73] Assignees: University of Florida, Gainesville, Fla.; l'Institut National de la Recherche Agronomique (INRA); le centre National de la Rechercho Scientifique (CNRS), both of Paris, France

[21] Appl. No.: 903,005

[22] Filed: Jun. 23, 1992

[51] Int. Cl.$^5$ .............. C12N 9/00; A01N 63/00; C12P 21/04; C07H 19/00

[52] U.S. Cl. .............. 435/183; 435/71.1; 435/71.3; 536/22.1; 536/23.1; 536/23.2; 536/23.7

[58] Field of Search ............ 435/71.1, 71.3, 183; 530/350, 412, 413, 414, 416, 417; 536/22.1, 23.1, 23.2, 23.7; 424/93 Q

[56] References Cited

PUBLICATIONS

Strongman et al "*Hirsutella longicolla* new species..." J. Invertebrate Pathol 55(1):11–16 1990.

Freifelder "Chromatography", *Physical Biochemistry* pp. 216–272 1982.

*Primary Examiner*—Robert A. Wax
*Assistant Examiner*—Hyosuk Kim
*Attorney, Agent, or Firm*—Spensley Horn Jubas & Lubitz

[57] ABSTRACT

A novel toxin of the genus Hirsutella which is useful in controlling invertebrate pests.

3 Claims, 3 Drawing Sheets

N-APKVTSRPKLDGREKPFKVDVATAQAQARKAGLT-C

FIG.1

TOXIC METABOLIC PRODUCT OF HIRSUTELLA SP.

BACKGROUND OF THE INVENTION

1. Field of the Invention

The present invention relates to a unique fungal toxin and its use in controlling invertebrate pests.

2. Description of Related Art

Insects and other pests are responsible for billions of dollars in loss of important agricultural crops every year. Therefore, it is of critical importance to find suitable protection from such pests for these plants. Traditionally, broad spectrum chemical pesticides have been used to protect the world's crops. Unfortunately, in addition to pests, other beneficial insects are often destroyed as well. Chemical pesticides may also have deleterious effects on humans or animals that have been exposed to them. Chemical pesticides can pollute the environment and can create health hazards to both agricultural workers and consumers. Also, because many pests develop resistance to chemical pesticides, these compounds are often rendered ineffective or must be utilized in resistance management strategies only.

The use of biological methods of pest control was first suggested in 1895, when a fungal disease was discovered in silkworms. Later, in 1940, spores of *Bacillus popilliae* were used to control the Japanese beetle. This was the first known successful use of biological pesticides.

In more recent years, considerable research has been done trying to develop biopesticides against agriculturally and medically important pests. In large part, these studies have focused on strains and toxins of *Bacillus thuringensis* (B.T.). However, in recent years reports have appeared that pests can develop resistance to various strains of B.T. and their toxins and other naturally occurring microbes, thereby demonstrating that pest control in the future must be diverse, such as by utilizing both chemical and biological methods in an integrated manner.

There is a need for more naturally occurring "biopesticides" which are safe to humans and animals yet toxic to agricultural pests. Biopesticides are often safer and ecologically more acceptable than chemical pesticides and there is a lower chance for the pests to develop resistance to naturally occurring biopesticides. This invention provides a novel, broad spectrum, naturally occurring mycoinsecticide.

The genus *Hirsutella* includes about 50 entomopathogenic species that attack a wide range of insects. The mononematous hyphomycete fungi, *Hirsutella thompsonii* var. *thompsonii*, *H. thompsonii* var. *vinacea* and *H. thompsonii synnematosa*, all produce hirsutellin A with similar toxicogenic activity.

In vivo, *Hirsutella thompsonii* and related species produce infective conidia on phialides arising from external mycelia growing from the host. Hyphae can emerge from cadavers through oral and anal openings, appendages, genital opening and at times through the body wall. Within the host, hyphae usually develop initially in the central area of the hemocoel as oval bodies and then become chain-like as they grow anteriorly or posteriorly along the inner body wall. In nature, these internal hyphae may break up and form multinucleate spherical chlamydospores. Host mortality appears to result from invasion of tissue by the fungal hyphae, while no toxicogenic activity has been reported. Although different naturally occurring biopesticides have been developed, none has been produced from the metabolites of Hirsutella spp. This invention addresses this need by providing a safe, naturally occurring biopesticide from Hirsutella spp. which has a broad spectrum insecticidal effect.

SUMMARY OF THE INVENTION

Recognizing the need to control invertebrate pests which avoids the use of traditional pesticides and their toxic side effects, the inventors searched for a novel biopesticide among the various invertebrate fungal pathogens. These efforts have culminated in the substantial purification and isolation of a novel toxin from the genus Hirsutella denoted hirsutellin A.

The hirsutellin A molecule has been characterized and found to possess a broad spectrum of activity with various invertebrate pests. These findings advantageously render routine the cloning of the hirsutellin A toxin polynucleotide thereby enabling the development of novel host systems for use as pest-controlling compositions and as sources of hirsutellin A polypeptide.

BRIEF DESCRIPTION OF THE DRAWINGS

FIG. 1 shows a 34 amino acid sequence which comprises a hirsutellin A polypeptide.

FIG. 2 shows toxicity of hirsutellin A via Contact and Residual exposure to the citrus rust mite.

DETAILED DESCRIPTION OF THE INVENTION

Figure 2A:
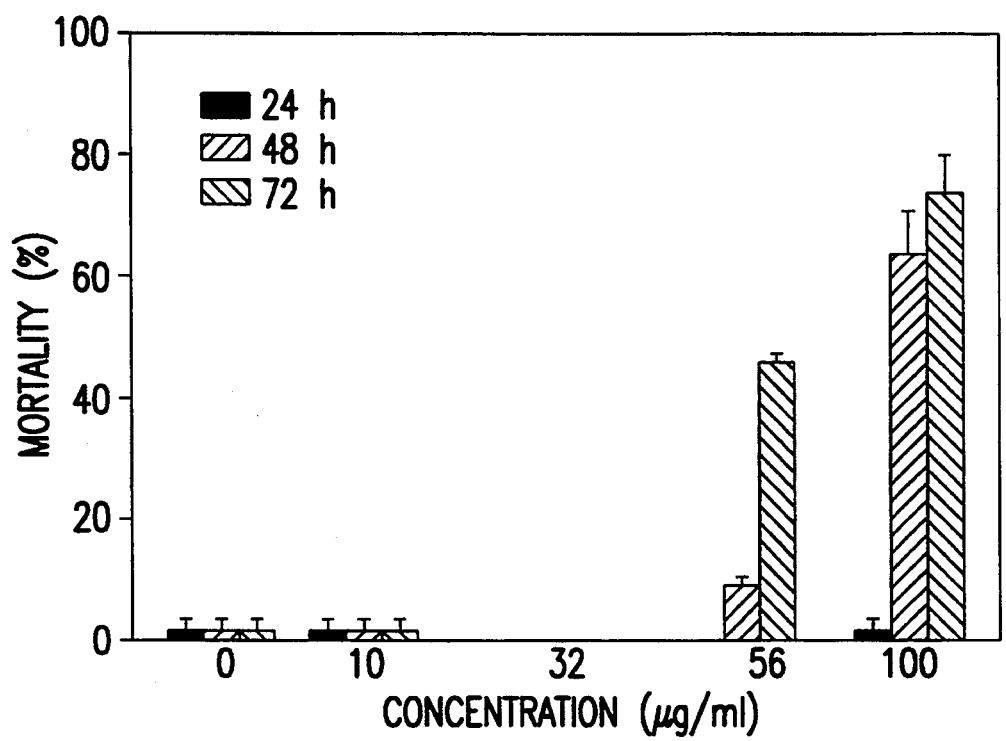
FIG. 2A shows residual toxicity of hirsutellin A to adult citrus rust mite at 24, 48, and 72 hours at 0, 10, 32, 56, and 100 $\mu$g/ml.

The present invention discloses the novel insecticidal mycotoxin protein hirsutellin A. This fungal metabolite is toxic to invertebrate pests. Treatment of adult insects or larvae with hirsutellin A protein is lethal. An advantage to the use of hirsutellin A is that pests can be controlled without the environmental and public safety hazards previously presented by chemical control agents.

The hirsutellin A of this invention is characterized by a monomeric basic protein with a molecular weight of 15 KD and a pI of 10.5., with heat sensitivity at 60° C. or greater after 15 minutes. Crude broth extracts of Hirsutella sp. grown in vitro in shake cultures, as well as purified hirsutellin A, exhibit toxicogenic activity in various insect species.

The exact mechanism of action for hirsutellin A toxicity is unknown. Injection of hirsutellin A into *Galleria mellonella* larvae results in alterations of the digestive tract, particularly the midgut and the malpighian tubules. Ultrastructural studies of organs and cells show strong cellular changes in the malpighian tubules. The pycnotic evolution of the nucleus, which displays large and dense aggregates of chromatin, is intense and many alterations are visible at the cytoplasmic level. The hyaloplasm shows a reduced electron density and mitochondria show obvious alterations.

The present invention provides substantially pure hirsutellin A polypeptide and method for producing. In addition, polynucleotide sequences encoding hirsutellin A or functional fragments of the polypeptide are included. Also provided is a method for controlling an invertebrate pest using a pest-controlling amount of hirsutellin A polypeptide.

The term "pest" refers to any agricultural invertebrate including, but not limited to, arthropods such as ticks, mites, lepidoptera, hemiptera, diptera (mosquitos), homoptera and coleopera (beetles). Other pests may include Plutella, Aedes, Galleria, Drosophila, Bombyx, Aphis and Eutetranychus.

The term "pest-controlling" or "pest controlling activity", used throughout the specification and in the claims include any pesticidal or pest inhibiting activities of a composition of the invention against a particular pest. These terms include killing as well as activities which cause such injury to the pest so as to inhibit the production or development of future progeny.

Amino acids referred to herein may be identified according to the following three-letter or one-letter abbreviations:

| Amino Acid | Three-Letter Abbreviation | One-Letter Abbreviation |
| --- | --- | --- |
| L-Alanine | Ala | A |
| L-Arginine | Arg | R |
| L-Asparagine | Asn | N |
| L-Aspartic Acid | Asp | D |
| L-Cysteine | Cys | C |
| L-Glutamine | Gln | Q |
| L-Glutamic Acid | Glu | E |
| L-Glycine | Gly | G |
| L-Histidine | His | H |
| L-Isoleucine | Ile | I |
| L-Leucine | Leu | L |
| L-Lysine | Lys | K |
| L-Methionine | Met | M |
| L-Phenylalanine | Phe | F |
| L-Proline | Pro | P |
| L-Serine | Ser | S |
| L-Threonine | Thr | T |
| L-Tryptophan | Trp | W |
| L-Tyrosine | Tyr | Y |
| L-Valine | Val | V |

The term "substantially pure" as used herein refers to hirsutellin A which is substantially free of other proteins, lipids, carbohydrates or other materials with which it is normally associated. The substantially pure hirsutellin A polypeptide yields a single major band of 15 kD on a non-reducing polyacrylamide gel. The purity of hirsutellin A can also be determined by amino-terminal amino acid sequence analysis. Hirsutellin A polypeptide includes functional fragments of the polypeptide, so long as hirsutellin A activity is retained. Therefore, smaller peptides containing the biological activity of hirsutellin A are included in the invention. Minor modifications of the hirsutellin A primary amino acid sequence may result in proteins which have substantially equivalent activity compared with hirsutellin A described in the invention. Such modifications may be deliberate, as by site-directed mutagenesis, or may be spontaneous. For example, more effective hirsutellin A molecules that may be produced by these modifications are included herein, as long as hirsutellin A activity still exists.

The present invention provides a method for producing substantially pure hirsultellin A. Procedures include those commonly used for the separation of protein substances including, for example, treatment of a sample containing hirsutellin A activity with common precipitants for proteins, followed by fractionation techniques such as ion exchange chromatography, affinity chromatography, molecular sieve chromatography, adsorption chromatography, ultrafiltration and various combinations thereof. Preferably, the method of the invention includes, a) a salt precipitation step, b) a step for removal of neutral and acidic proteins, such as an ion exchange step, and c) exclusion chromatography.

Preferably, the sample containing toxin is produced by growth of a fungus which produces hirsutellin A such as *Hirsutella thompsonii*, in yeast extract containing medium such as Czapek-Dox broth at 25° C. The sample containing hirsutellin A activity is salt precipitated, preferably with ammonium sulfate. After partial precipitation, the material is desalted using gel filtration, for example, with Sephadex G-25, followed by ion exchange chromatography. The material is treated with an anion exchange resin with a diethylaminomethyl (DEAE) or a diethyl-(2-hydroxypropyl)aminoethyl (QAE) functional group, preferably a diethylaminomethyl group. DEAE is a weak anion exchange resin and is preferably to stronger anion exchange resins such as QAE agarose for the present invention. The treatment conditions, e.g., a solution of about pH 8.0 and a linear salt gradient of about 0 to 0.3M, are such that the hirsutellin A activity is not adsorbed to the support.

Hirsutellin A activity can be determined by its insecticidal effect. One suitable assay for hirsutellin A activity includes that described in EXAMPLE 3, which involves the injection of the hirsutellin A containing solution into Lepidopteran larvae.

In a preferred embodiment, the pooled fractions containing partially purified hirsutellin A are treated next with a cation exchange material with a carboxymethyl or sulphopropyl functional group, preferably a carboxymethyl group. Carboxymethyl resin is preferably to the stronger cation ion exchange resins, such as those with sulphopropyl groups. The treatment conditions, e.g., a solution of about pH 5.0 and a salt concentration of about 0.05M to 0.5M, are such that the hirsutellin A activity initially adsorbed to the support, is then eluted at a salt concentration of about 0.3M. The resulting material is tested for hirsutellin A activity as described above and as described in EXAMPLE 3.

The unbound fractions containing hirsutellin A activity can be further purified by gel filtration using, for example, any commerically available sizing gel such as biogel P10 (Biorad) which has a molecular weight fractionation range of about 1,500 to 20,000 daltons. The hirsutellin A containing fractions after treatment with the gel are then subjected to SDS PAGE under suitable conditions and the gel slice containing hirsutellin A activity is recovered. SDS PAGE is performed according to the method of Laemmli, et al., (Nature, 227:680, 1970) and is a technique well known to those in the art. Variations in conditions which are within a suitable range are understood to be encompassed within the purification procedure.

The hirsutellin A activity-containing fraction from the SDS PAGE is subjected to reverse phase HPLC and eluted with acetonitrile. The hirsutellin A which is obtained is substantially pure to permit N-terminal amino acid sequencing. The toxic solution is dried under vacuum and redissolved in a small volume of acetonitrile 95% +TFA (0.08%). The concentrated sample is then introduced in a sequencer connected to a phenylthiohydantoine (PTH) analyzer.

A preferred embodiment of the invention comprises the polypeptide, APKVTSRPKLDGNEKPFKVDV (SEQ. I.D. No. 1) and conservative variations of this peptide. The term "conservative variation" as used herein denotes the replacement of an amino acid residue by another, biologically similar, residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that the substituted polypeptide retain the pest controlling activity of the unsubstituted polypeptide.

Antibodies provided in the present invention are immunoreactive with hirsutellin A polypeptide or fragments thereof. Polyclonal antibodies are prepared by immunization of an animal, e.g., rabbit, with an immunogenic sample of hirsutellin A followed by purification of the antibody by methods well known in the art. Antibody which consists essentially of pooled monoclonal antibodies with different epitopic specificities, as well as distinct monoclonal antibody preparations, are provided. Monoclonal antibodies are made from antigen containing fragments of the protein by methods well known in the art (Kohler, et al., Nature, 256:495, 1975). The term "antibody" as used in this invention is meant to include intact molecules as well as fragments thereof, such as Fab and F(ab')$_2$, which are capable of binding the epitopic determinant.

The antibodies of the invention can be used in immunoaffinity chromatography for the isolation of sequences containing the hirsutellin A activity of the present invention. One way by which such immunoaffinity chromatography can be utilized is by the binding of the antibodies of the invention to CNBr-Sepharose-4B or Tresyl activated Sepharose (Pharmacia). These solid phase-bound antibodies can then be used to specifically bind sequences containing hirsutellin A activity from mixtures of other proteins to enable isolation and purification thereof. Bound hirsutellin A sequences can be eluted from the affinity chromatographic material using techniques known to those of ordinary skill in the art such as, for example, chaotropic agents, low pH, or urea.

The invention provides polynucleotides encoding the hirsutellin A protein. These polynucleotides include DNA, cDNA and RNA sequences which encode hirsutellin A. It is understood that all polynucleotides encoding all or a portion of hirsutellin A are also included herein, so long as they encode a polypeptide with hirsutellin A activity. Such polynucleotides include both naturally occurring and intentionally manipulated polynucleotides. For example, hirsutellin A may be subjected to site-directed mutagenesis. The polynucleotides of the invention include sequences that are degenerate as a result of the genetic code. There are only 20 natural amino acids, most of which are specified by more than one codon. Therefore, as long as the amino acid sequence of hirsutellin A is unchanged, or although changed retains hirsutellin A activity, all degenerate nucleotide sequences are included in the invention.

DNA sequences of the invention can be isolated by several techniques known in the art. These include, but are not limited to: 1) hybridization of probes to genomic or cDNA libraries to detect shared nucleotide sequences, and 2) antibody screening of expression libraries to detect shared structural features.

Screening procedures which rely on nucleic acid hybridization make it possible to isolate any gene sequence from any organism, provided the appropriate probe is available. For example, oligonucleotide probes, which correspond to a part of the sequence encoding the protein in question, can be synthesized chemically. This requires that short, oligopeptide stretches of amino acid sequence must be known. Preferably, the oligonucleotide probe of the invention encodes a consecutive sequence from about four to about thirty-four amino acids of the amino acid sequence APKVTSRPKLDGREKPFKVDVATAQAQARKAGLT (SEQ. I.D. No. 2) including any conservative variations. A preferred oligonucleotide probe encodes a consecutive sequence of the amino acids EKPFKV, including any conservative variations of this peptide. The DNA sequence encoding the protein can be deduced from the genetic code, however, the degeneracy of the code must be taken into account. It is possible to perform a mixed addition reaction when the sequence is degenerate. This includes a heterogenous mixture of denatured double-stranded DNA. For such screening, hybridization is preferably performed on either single-stranded DNA or denatured double-stranded DNA. This is especially useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by hybridization of the target DNA to the single probe in the mixture which is its complement (Wallace, et al., Nucleic Acid Research, 9:879, 1981).

A cDNA expression library, such as λgt11, can be screened indirectly for hirsutellin A peptides having at least one antigenic epitope, using antibodies specific for hirsutellin A. Such antibodies can be either monoclonal or polyclonal and used to detect an expression product indicative of the presence of hirsutellin A cDNA.

A hirsutellin A cDNA library can also be screened by injecting different cDNAs into oocytes. After expression of the cDNA gene products occurs, the presence of the specific cDNA gene product can be identified by antibody screening with antibody specifically immunoreactive with hirsutellin A polypeptide, for example. Alternatively, functional assays for hirsutellin A toxicogenic activity could be performed to identify Hirsutellin A producing oocytes.

Specific DNA sequences encoding hirsutellin A can also be obtained by: (1) isolation of double-stranded DNA sequences from genomic DNA; (2) chemical manufacture of a DNA sequence to provide the necessary codons for the polypeptide of interest; and (3) in vitro synthesis of a double-stranded DNA sequence by reverse transcription of mRNA isolated from a eukaryotic donor cell, resulting in a cDNA, or complimentary DNA.

Synthesis of DNA sequences is frequently the method chosen when the entire sequence of amino acid residues of the desired polypeptide product is known. When the entire sequence of amino acid residues of the desired polypeptide is not known, the direct synthesis of DNA sequences is not possible and the method of choice is the formation of cDNA sequences. Among the standard procedures for isolating cDNA sequences of interest is the formation of plasmid or bacteriophage based cDNA libraries in which mRNA is reverse transcribed from donor cells with a high level of genetic expression. When used in combination with polymerase chain reaction (PCR) technology, less common mRNA species (cDNA) can be cloned as well. When significant portions of the amino acid sequence of a polypeptide are known, labeled single or double-stranded DNA or RNA probes which represent a sequence present in the target cDNA, may be used in DNA/DNA hybridization procedures which are performed on cloned copies of the cDNA which have been denatured into a single-stranded form (Jay, et al., Nucleic Acid Research, 11:2325, 1983).

Since the novel DNA sequences of the invention encode a unique sequence of hirsutellin A, it is now a routine matter to prepare, subclone, and express smaller polypeptide fragments of DNA from this or corresponding DNA sequences. Alternatively, by utilizing the DNA fragments disclosed herein which define the unique hirsutellin A polypeptide of the invention, it is possible, in conjunction with known techniques, to determine the DNA sequences encoding the entire hirsutellin A toxin. Such techniques are described in U.S. Pat. Nos. 4,394,443 and 4,446,235 which are incorporated herein by reference.

The polypeptide resulting from expression of a DNA sequence of the invention can be further characterized as being free from association with other eukaryotic polypeptides or other contaminants which might otherwise be associated with the polypeptide in its natural cellular environment.

Isolation and purification of microbially expressed polypeptides provided by invention may be by conventional means including, preparative chromatographic separations and immunological separations involving monoclonal and/or polyclonal antibody preparation.

For purposes of the present invention, hirsutellin A polypeptides which are homologous to those of the invention can be identified by structural as well as functional similarity. Structural similarity can be determined, for example, by assessing polynucleotide strand hybridization or by screening with antibody, especially a monoclonal antibody, which recognizes a unique epitope present on the hirsutellin A polypeptides of the invention. When hybridization is used as criteria to establish structural similarity, those polynucleotide sequences which hybridize under stringent conditions to the polynucleotides of the invention are considered to be essentially the same as the polynucleotide sequences of the invention.

A wide variety of ways are available for introducing a polynucleotide expressing a hirsutellin A toxin into the microorganism host under conditions which allow for stable maintenance and expression of the gene. DNA constructs are available which include the transcriptional and translational regulatory signals for expression of the hirsutellin A polynucleotide; the toxin gene under their regulatory control and a DNA sequence homologous with a sequence in the host organism, whereby integration will occur; and/or a replication system which is functional in the host, whereby integration or stable maintenance will occur.

The transcriptional initiation signals will include a promoter and a transcriptional initiation start site. In some instances, it may be desirable to provide for regulative expression of the hirsutellin A polynucleotide, where expression of the toxin will only occur after release into the environment. This can be achieved with operators or a region binding to an activator or enhancers, which are capable of induction upon a change in the physical or chemical environment of the host. For example, a temperature sensitive regulatory region may be employed where the organisms may be grown up in the laboratory without expression of a toxin, but upon change in the growth conditions or environment, expression would begin. Other techniques may employ a specific nutrient medium in the laboratory, which inhibits the expression of the toxin, where the nutrient medium in the later environment would allow for expression of the toxin. For translational initiation, a ribosomal binding site and an initiation codon will be present.

Various manipulations may be employed for enhancing the expression of the mRNA, particularly by using an active promoter, as well as by employing sequences, which enhance the stability of the mRNA. The initiation and translational termination region will involve stop codon(s), a terminator region, and optionally, a polyadenylation signal.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

A marker structural gene may be present which provides for selection of those hosts which have been modified or transformed. The marker will normally provide for selective advantage, for example, providing for biocide resistance, for example, resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, for example, siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the Tac promoter, the naturally-occurring promoters associated with the toxin gene, where functional in the host. See, for example, U.S. Pat. Nos. 4,332,898, 4,352,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSFIO10, pR01614, and the like. (See, for example Olson et al., J. Bacteriol. 150:6069, 1982, and Bagdasarian et al., Gene 16:237, 1981, and U.S. Pat. Nos. 4,356,270, 4,362,817, and 4,371,625.)

The hirsutellin A polynucleotide can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, as described above. Where integration is desired, the plasmid will desirably include a sequence homologous with the host genome.

The transformants can be isolated in accordance with conventional techniques usually employing selection of the desired organism as against unmodified organisms or transferring organisms, when present. The transformants then can be screened for pesticidal activity.

Suitable host cells, where the pesticide-containing cells will be treated to prolong the activity of the toxin in the cell where the treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to limit any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the hirsutellin A polynucleotide into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., *Aureobasidium* sp., *Saccharomyces* sp., and *Sporobolomyces* sp.; phylloplane organisms such as *Pseudomonas* sp., *Erwinia* sp. and *Flavobacterium* sp.; or such other organisms as *Escherichia, Lactobacillus* sp., *Bacillus* sp., and the like. Specific organisms include *Pseudomonas aeruginosa, Pseudomonas fluorescens, Saccharomyces cerevisiae, Bacillus thuringiensis, Escherichia coli, Bacillus subtilis*, and the like.

In general, expression vectors containing promotor sequences which facilitate the efficient transcription of the inserted genetic sequence are used in connection with the host. As described above, biologically functional viral or plasmid DNA vectors caable fo expression and replication in a host are known in the art. Such vectors are used to incorporate hirsutellin A encoding DNA sequences of the invention. Expression vectors typically contain an origin of replication, a promoter, and a terminator, as well as specific genes which are capable of providing phenotypic selection of the transformed cells.

Transformation of the host cell with the recombinant DNA may be carried out by conventional techniques well known to those skilled in the art. Where the host is prokaryotic, such as *E. coli*, competent cells which are capable of DNA uptake can be prepared from cells harvested after exponential growth and subsequently treated by the $CaCl_2$ method using procedures well known in the art. Alternatively, $MgCl_2$ or RbCl could be used.

Where the host used is a eukaryote, various methods of DNA transfer can be used. These include transfection of DNA by calcium phosphate-precipitates, conventional mechanical procedures such as microinjection or electroporation, insertion of a plasmid encased in liposomes, or the use of viral vectors.

Eukaryotic host cells may also include yeast. For example, DNA can be expressed in yeast by inserting the DNA into appropriate expression vectors and introducing the product into the host cells. Various shuttle vectors for the expression of foreign genes in yeast have been reported (Heinemann, J. et al., Nature, 340:205, 1989; Rose, M. et al., Gene, 60:237, 1987).

Isolation and purification of microbially expressed protein, or fragments thereof provided by the invention, may be carried out by conventional means including preparative chromatography and immunological separations involving monoclonal or polyclonal antibodies. Antibodies provided in the present invention are immunoreactive with the hirsutellin A polypeptides of the invention. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., Nature, 256:495, 1975; Current Protocols in Molecular Biology, Ausubel, et al., ed., 1989).

Minor modifications of the hirsutellin A primary amino acid sequence may result in polypeptides which have substantially equivalent activity compared to the hirsutellin A polypeptides described herein. Such modifications may be deliberate, as by site-directed mutagenesis, or may be spontaneous. All proteins produced by these modifications are included herein as long as hirsutellin A pest controlling activity is present.

Compositions of the invention include those in which an organism is genetically modified to contain polynucleotide encoding hirsutellin A polypeptides. Treatment of the organism, for example, a microbe, can be by chemical or physical means, or by a combination of chemical and/or physical means, so long as the technique does not deleteriously affect the properties of the toxin, nor diminish the cellular capability in protecting the toxin. Examples of chemical reagents are halogenating agents. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink protein and could inhibit processing of the proform of a polypeptide pesticide. The method of inactivation or killing retains at least a substantial portion of the bio-availability or bioactivity of the toxin.

The cellular host containing the hirsutellin A polypeptide insecticidal gene may be grown in any convenient nutrient medium, where the DNA construct provides a selective advantage, providing for a selective medium so that substantially all or all of the cells retain hirsutellin A gene. These cells may then be harvested in accordance with conventional ways. Alternatively, the cells can be treated prior to harvesting.

The pest-controlling agent of the present invention may be prepared as dusts, water dispersions, emulsions and solutions. They may comprise accessory agents such as dust carriers, solvents, emulsifiers, wetting and dispersing agents, stickers, deodorants, and masking agents (see, for example, Encyclopedia of Chemical Technology, Vol. 13, pp. 416, et seq.).

Dusts generally will contain low concentrations, 0.1–20% of hirsutellin A, although ground preparations may be used and diluted. Carriers commonly include sulfur, silcon oxides, lime gypsum, talc, pyrophylite, bentonite, kaolins, attapulgite, and volcanic ash. Selection of the carrier may be made on the basis of compatibility with the desired pest control composition (including pH, moisture content, and stability), particle size, abrasiveness, absorbability, density, wettability and cost. The agent of the invention, alone or in combination, and eluent is made by a variety of simple operations such as milling, solvent impregnations, fusing, and grinding. Particle sizes usually range from 0.5–4.0 microns in diameter.

Wettable powders may be prepared by blending the hirsutellin A of the invention in high concentrations, usually from 15–80% with a dust carrier such as bentonite which wets and suspends properly in water. Twenty-two percent of a surface-active agent is usually added to improve the wetting and suspendability of the powder.

Hirsutellin A may also be used in granules, which are pelleted mixtures of the agents, usually at 2.5–20%, and a dust carrier, e.g., adsorptive clay, bentonite or diatomaceous earth, and common within particle sizes of 250–590 microns. Granules may be prepared by impregnations of the carrier with a solution or slurry of the organism and may be used principally for soil applications or for mosquito larvae treatment The hirsutellin A may also be applied in the form of an emulsion, which comprises a solution of hirsutellin A in water-immisicible organic solvents, commonly at 15–50%, with a few percent of surface active agent to promote emulsification, wetting, and spreading. The choice of solvent is predicated upon solubility, safety to plants and animals, volatility, flammability, safety to plants and animals, compatibility, odor and cost.

The hirsutellin A of the present invention may also be applied depending on the properties of the particular pest-controlling compound, the habits of the pest to be controlled, and the site of the application to be made. It may be applied by spraying, dusting or fumigation.

Sprays are a common means of application and generally will involve the use of water as the principal carrier, although volatile oils may also be used, The pest-controlling agents of the invention may be used in dilute sprays or in concentrate sprays, and the amount of carrier to be applied is reduced. The use of concentrate and ultra low volume sprays will allow the use of atomizing nozzles producing droplets of 30–80 microns in diameter.

Aerosols may also be used to apply hirsutellin A. Aerosols are applied by atomizing amounts of liquified gas dispersion or bomb, but can be generated on a larger scale by rotary atomizers or twin-fluid atomizers. Carriers used as aerosols or liquified gas may include mineral spirits, ethanol, isopropanol, deionized water, and hydrocarbon propellants, such as isobutane, n-butane, and propane or nonflammable fluorinated hydrocarbon propellants, or compressed gases, such as nitrogen, carbon dioxide, or nitrous oxide. The aerosol composition will typically comprise about 0.001–10% hirsutellin A of the invention, and the remainder being aerosol or liquified gas ingredients (The Science and Technology of Aerosol Packaging, John Wiley & Sons, 1974).

The following examples are intended to illustrate but not limit the invention. While they are typical of those that might be used, other procedures known to those skilled in the art may alternatively be used.

EXAMPLE 1

PURIFICATION OF HIRSUTELLIN A

A. CRUDE FILTRATE PRODUCTION

Solid cultures of H. thompsonii var. thompsonii (ATCC 24874) were grown on soil fungus medium (SFM) for 5 days in 90 mm petri plates at 28° C. An inoculum was prepared by washing the conidia from the surface of a sporulating aerial mycelial mat of a given number of petri plates with sterile distilled water and then concentrating the conidial suspension by centrifugation.

Broth culture containing Czapek-Dox medium plus yeast extract at 10 g/l were prepared in Erlenmeyer flasks. Each flask was inoculated with a conidial suspension at $4 \times 10^6$ conidia per 35 ml of broth. Flasks were then placed randomly on a gyrator water bath shaker maintained at 25° C. Cultures were agitated at 100 RPM for 10 days. After incubation, the mycelial biomass was separated from the supernatant via filtration through cheesecloth and filter paper. Each crude broth was then filtered again through a 0.45 $\mu$m filter to ensure sterility and stored at 4° C. or lyophilized for extended storage.

B. INITIAL PRECIPITATION AND CONCENTRATION

The following strategy was developed to separate the different toxic metabolites of *Hirsutell thompsonii* var. thompsonii as pure compounds. This purification procedure was developed by initially adding ammonium sulfate to the crude filtrate to precipitate and concentrate proteins, desalting by gel filtration on Sephadex G-25 and applying different steps of ion exchange and exclusion chromatography.

The different fractions collected were analyzed for their absorption at 280 nm. These fractions were screened for biological activity by injection of 8 $\mu$l of each solution in larvae (L6) of the experimental host, *Galleria mellonella*. The contents of each fraction were also analyzed by SDS PAGE electrophoresis to monitor the evolution of the purification process.

The proteins of the crude filtrate were precipitated by addition of ammonium sulfate, at a concentration of 0.76 mg/ml (90% of saturation). After a storage of 15 hr at 4° C., the pellet of precipitated proteins was collected by centrifugation for 1 hr at 8500 rpm, and the supernatant was discarded. The pellet was dissolved in a small amount of distilled water (1/30 to 1/40 of the volume of filtrate) to obtain an increase of concentration.

C. GEL FILTRATION ON SEPHADEX G-25

In a next step, exclusion liquid chromatography with Sephadex G-25 was performed for desalting the precipitate.

The concentrated solution prepared above was applied o a 2.5×25 cm column and eluted with 0.05M Tris-HCl buffer, pH 8. Fractions of 7.5 ml were collected, analyzed for absorption at 280 nm, and tested for biological activity by injection of 0.8 $\mu$l of each of these solutions to L6 larvae of the lepidopteran insect *Galleria mellonella* (200 mg of mean body weight).

Among these fractions (F) only F1, 2 and 3, collected immediately after the void volume and containing the macromolecules excluded from the gel (MW cut-off=5000D), showed an insecticidal effect. A pool of F1, 2 and 3, with a total concentration in proteins of 500 $\mu$g/ml (Biorad method of dosage) induced a rapid rate of mortality in 100% of the injected larvae.

D. ION EXCHANGE CHROMATOGRAPHY WITH DEAE

Ion exchange chromatography was performed by DEAE-Trisacryl, a weak anion exchanger.

Fractions 1–3 eluted from Sephadex G-25 were filtrated on membranes of a porosity of 0.2$\mu$, and then applied to DEAE-Trisacryl column (1×16 cm). The column was equilibrated with 0.05M Tris-HCl buffer, pH 8. This column was washed with the same buffer, and the bound material was eluted with a 60 ml 0 to 0.3M linear NaCl gradient in the same buffer, at a flow rate of 50 ml/hr. Fractions of 3.5 ml were collected, and the absorbance at 280 nm was recorded.

A first peak, corresponding to non-adsorbed material, was obtained during washing, at the level of fractions F2, 3 and 4. A pool of these fractions (200 $\mu$g/ml of proteins) induced (by injection) a rate of mortality of 85–95% in the G. *mellonella* larvae. The intoxicated larvae showed a characteristic aspect; they were swollen and displayed small dispersed melanized spots on their cuticle.

At the beginning of the elution of the NaCl gradient a second peak of compounds previously bound to DEAE appeared, but detached quickly. Fraction F15, whose concentration in proteins was 200 $\mu$g/ml, also caused a rate of lethality of 90%. The larvae were not swollen, and the brownish color of the cuticle was more apparent.

E. ION EXCHANGE CHROMATOGRAPHY WITH A CATION EXCHANGER

Fractions 1–3 from DEAE were applied to a carboxymethyl-Trisacryl column (1×16 cm) equilibrated with a 0.05M sodium acetate buffer, pH 5. The column was washed with this buffer, and the bound material was eluted in a first step with 0.1M NaCl in the same buffer, and in a second step by elution with a 0.2 to 0.4M NaCl gradient. During elution of the gradient, a peak was obtained at a NaCl concentration of 0.3M, at the level of fraction 50. Among the fractions tested for their biological activity, only those corresponding to this peak were toxic, causing a mortality at 100% when injected into Galleria larvae. Hirsutellin A was therefore present in these fractions. However, this material was not pure as SDS-PAGE electrophoresis of these solutions revealed two bands after staining of gels with Coomassie brilliant blue.

F. EXCLUSION CHROMATOGRAPHY

The native fractions collected by ion exchange chromatography on carboxymethyl-Trisacryl were dialyzed against distilled water and then freeze-dried. The freeze-dried powder was dissolved in 0.05M Tris-HCl buffer, pH 8, in conditions to increase the concentration to ×40 for exclusion chromatography. Gel permeation runs were then performed with Biogel P 10, quality medium (Biorad) (fractionation range: 1500–20000 D).

During these experiments, the concentrated solution was applied to a biogel column (1×100 cm), and eluted with 0.05M Tris-HCl buffer, pH 8, at a flow rate of 15 ml/hr. Fractions of 1.5 ml were collected.

When these samples were analyzed, only one small peak was observed which eluted approximately the same as Cytochrome C (MW=12300). This fraction was very active as injection caused 100% mortality in *G. mellonella* larvae (see EXAMPLE 2B).

SDS-PAGE revealed only one band, even after silver staining (Biorad), and comparison with the MW standards showed that the MW of the components(s) of this band was about 15kD. When isoelectrofocusing was performed with a flat bed apparatus and Servalyt Precotes (Serva) 3-11 it also appeared as only one band. The pI was 10.5 according to the comparison with markers (Serva). When the same sample was submitted successively to isoelectrofocusing and to SDS-PAGE electrophoresis, there was again only one spot on the gel, thereby showing that the hirsutellin A was purified.

EXAMPLE 2

CHARACTERIZATION AND CLONING OF HIRSUTELLIN A

Column chromatography, electrophoresis, and isoelectrofocusing studies described above showed that hirsutellin A is a basic macromolecular monomeric protein with a molecular weight of 15 kD, an isoelectric point (pI) of 10.5. The purity of hirsutellin A was confirmed via HPLC and the composition of its amino acids determined. Determination of the sequence of amino acids of the NH-terminal portion of the hirsutellin A molecule was based on the Phenylthiohydantoine (PTH) method of Edman, et al. (Europ. J. Biochem., 1:80, 1967). It was performed with a gaseous phase sequencer connected to a PTH analyzer. The sequence of the first 34 amino acids of the NH-terminal part of the hirsutellin A molecule obtained by this method has been defined in FIG. 1. Search via a computer data base (C.I.T.I.2) did not reveal a significant degree of homology between hirsutellin A and other known proteins. In addition, research designed to identify a glycosylated fraction in hirsutellin A has proven negative. EXAMPLE 3

TOXICITY OF HIRSUTELLIN A

A. TOXICITY OF HIRSUTELLIN A TO *Galleria mellonella* LARVAE

To test the toxicity of hirsutellin A to larvae (L6) of *G. mellonella*, three concentrations of toxin, 25, 50 and 100 μg/ml, corresponding to final doses of 1,2 and 4 μg/g of body weight, respectively, were prepared and 8 μl of each treatment injected into the proleg of 20 larvae/replicate. A Tris buffer solution injection was performed as a control. Each treatment was replicated three times. Larval mortality was recorded daily.

All concentrations of hirsutellin A killed 100% of the larvae; however, the $LT_{50}$ increased with a decrease in dose. The $LT_{50}$ was 8.8±1.4, 17.1±1.8 and 24.2±2.0 at 100, 50 and 25 μg/ml, respectively. There was no mortality in the control (TABLE 1).

TABLE 1

MEAN PERCENT MORTALITY TO
*Galleria mellonella* LARVAE (L6)
FOLLOWING INJECTION OF DIFFERENT
CONCENTRATIONS OF HIRSUTELLIN A

| Dosage (μg/ml) | Mean % Mortality; Days Post-Treatment | | | | | | | $LT_{50}$ |
|---|---|---|---|---|---|---|---|---|
| | 4 | 5 | 10 | 15 | 20 | 25 | 30 | |
| 25 | 0.0 | — | 0.0 | 6.7 | 40.0 | 73.3 | 100.0 | 24.2 ± 2.0 |
| 50 | 0.0 | 7.5 | 35.0 | — | 80.0 | 100.0 | — | 17.1 ± 1.8 |
| 100 | 18.0 | 45.0 | 63.6 | 100.0 | — | — | — | 8.8 ± 1.4 |
| Control | 0.0 | 0.0 | 0.0 | 0.0 | 0.0 | 0.0 | 0.0 | — |

B. TOXICITY OF HIRSUTELLIN A TO NEONATAL *Aedas aegypti* LARVAE

To test the toxicity of hirsutellin A to neonatal mosquito larvae of *Aedes aegypti*, different concentrations of toxin, 0, 5, 10, 15 and 20 μg/ml, in 200 μl of water were placed into microtitration plates. A control containing only water was included. Each treatment was replicated three times. Twenty-four vigorous neonatal larvae were placed into each well under continuous exposure.

Larval mortality increased with an increase in toxin dosage. At 5 and 10 μg/ml, larval mortality reached 90% after 48 hr and 100% by 72 hr post-inoculation. Virtually no mortality was recorded from the control.

C. TOXICITY OF HIRSUTELLIN A TO *Plutella xylostella* CELL LINE

To test the toxicity of hirsutellin A on *Plutella xylostella* cells produced in tissue culture, different concentrations of toxin (0, 0.5, 1.0, 2.5, 5.0 and 10.0 μg/ml) were added via dilution to achieve a given test concentration in 2 ml of tissue culture medium containing $2 \times 10^5$ cells. A control containing cells in tissue culture media only was included. Living and dead cells per day were determined by staining with Trypan blue and the number of live cells at 1, 2, 3, 4 and 5 days was recorded (TABLE 2).

The growth rate of *P. xylostella* cells is tissue culture declined with an increase in concentration of hirsutellin A. At 10 μg/ml, all cells were killed after 2 days.

TABLE 2

| Toxin Conc. (μg/ml) | No. Live Cells/ml; Days Post-Treatment[a] | | | | | |
|---|---|---|---|---|---|---|
| | 0 | 1 | 2 | 3 | 4 | 5 |
| 0.0 | 2.0 | 5.5 | 6.4 | 8.6 | 9.0 | 12.0 |
| 0.5 | 2.0 | 4.0 | 6.9 | 8.3 | 9.8 | 9.1 |
| 1.0 | 2.0 | 4.7 | 7.3 | 7.8 | 9.4 | 9.7 |
| 2.5 | 2.0 | 2.6 | 3.3 | 3.1 | 3.8 | 3.4 |
| 5.0 | 2.0 | 2.1 | 2.2 | 2.2 | 2.2 | 2.5 |
| 10.0 | 2.0 | 1.7 | 3.2 | 0.0 | 0.0 | 0.0 |

[a]Live cells counted in hemocytometer after staining with Trypan blue × $10^5$

D. TOXICITY OF HIRSUTELLIN A VIA CONTACT AND RESIDUAL EXPOSURE TO THE CITRUS RUST MITE

Figure 2B:
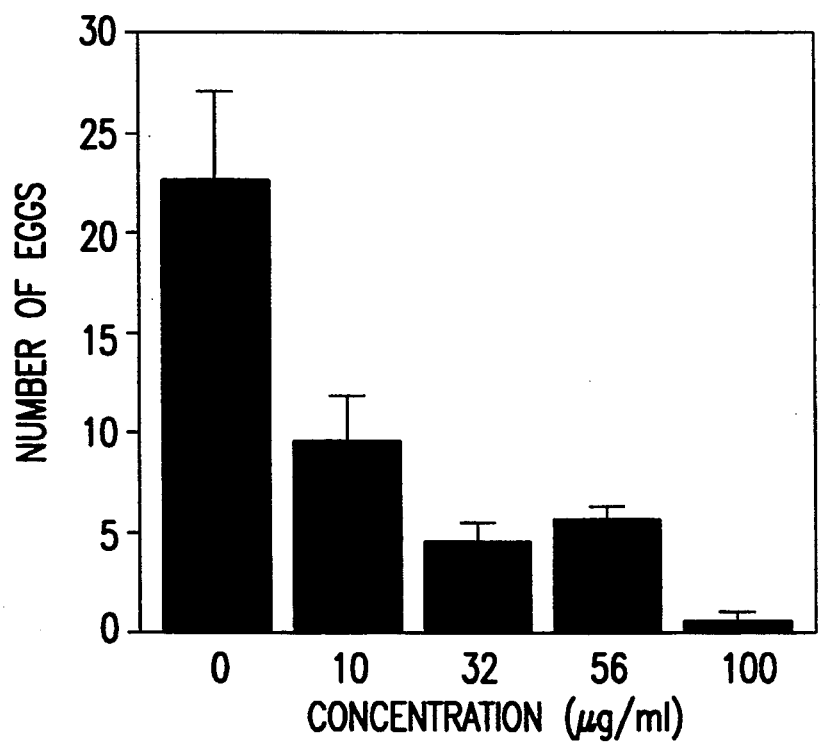
FIG. 2B shows egg production on the leaves after 72 hours following residual application of hirsutellin A.
Figure 2C:
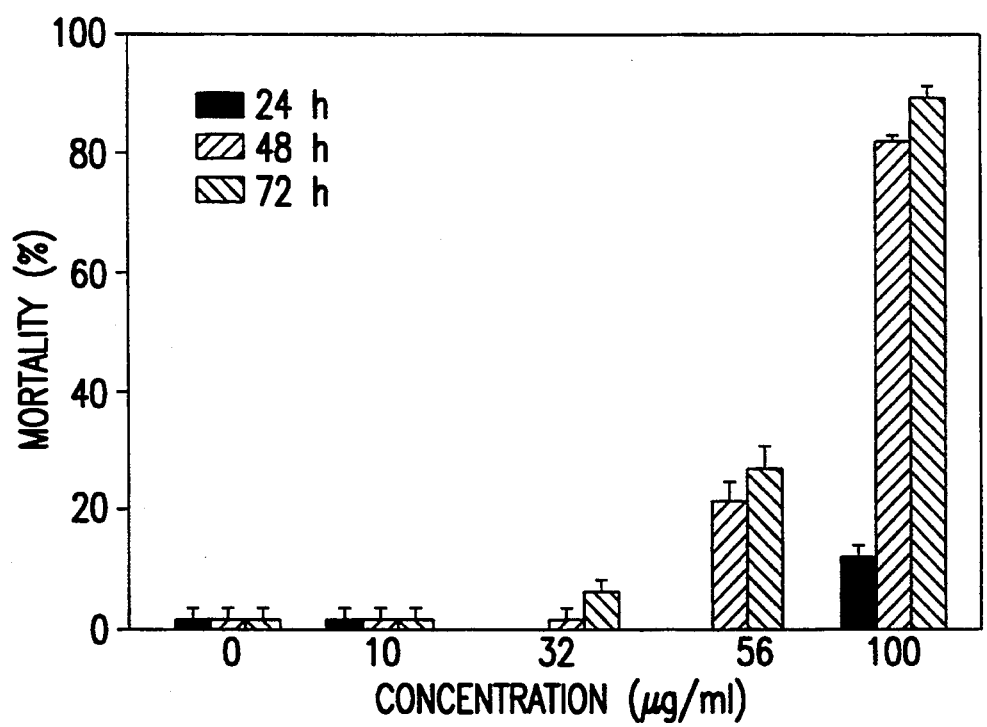
FIG. 2C shows contact and residual toxicity of hirsutellin A to adult citrus rust mite.
Figure 2D:
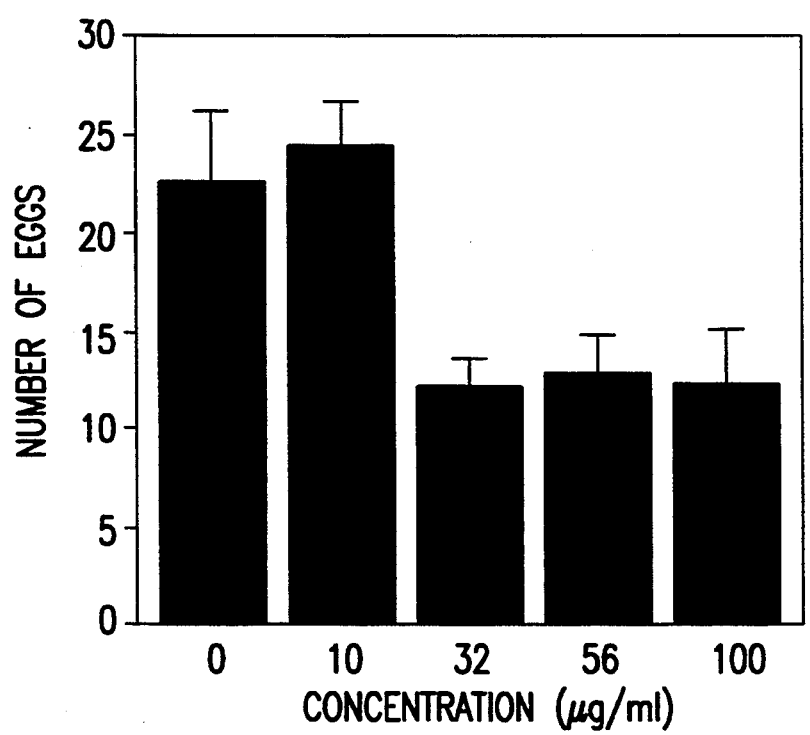
FIG. 2D shows egg production after 72 hours following contact and residual application of hirsutellin A.

Citrus rust mite (CRM), *Phyllocoptruta oleivora*, were reared on Sunburst mandarin citrus seedlings kept under plexiglass cages. Residual+contact (R+C) and residual (R) activity of hirsutellin A was tested at 0, 10, 32, 56 and 100 μg of toxin/ml. For determining R+C activity, citrus leaves were first placed on a wet cotton pad in an open Petri dish. Tanglefoot was then placed around the perimeter of leaves and 30 adult CRM mites were transferred to each leaf. About 2 ml of hirsutellin A at five concentrations were sprayed on each of four leaves using Potter tower. For determining R activity, leaves were sprayed with different concentrations of hirsutellin A before transferring the mites. Dishes were confined to a closed plastic container and held in a temperature cabinet at 25° C. +1° C. and photoperiod of 15 hr. Mortality was evaluated 24, 48 and 72 hr after infestation. The number of eggs found on each leaf surface was recorded at 72 hr (FIG. 2).

Good biological activity against CRM was observed 48 hr after infestation at 100 μg/ml. Interestingly, hirsutellin A also showed some effect on mite physiology because, at lower concentrations where low mortality was detected, oviposition was significantly reduced in comparison to the control. The higher number of eggs recorded in the R+C bioassay compared to the R bioassay was probably because some eggs were laid on the leaf before the application of the toxin.

Although the invention has been described with reference to the presently preferred embodiment, it should be understood that various modifications can be made without departing from the spirit of the invention. Accordingly, the invention is limited only by the following claims.

---

---

What is claimed is:

1. Substantially pure hirsutellin A polypeptide having insecticidal properties.

2. The hirsutellin A polypeptide of claim 1, wherein the polypeptide has a molecular weight of approximately 15 KD and a pL of approximately 10.5.

3. The polypeptide of claim 1 which comprises the amino acid sequence of Sequence ID No. 1 or Sequence ID No. 2 and conservative variations thereof.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 21 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..21

( x i ) SEQUENCE DESCRIPTION: SEQ ID NO:1:

Ala Pro Lys Val Thr Ser Arg Pro Lys Leu Asp Gly Arg Glu Lys Pro
1               5                   10                  15

Phe Lys Val Asp Val
            20

( 2 ) INFORMATION FOR SEQ ID NO:2:

( i ) SEQUENCE CHARACTERISTICS:
( A ) LENGTH: 34 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..34

( x i ) SEQUENCE DESCRIPTION: SEQ ID NO:2:

Ala Pro Lys Val Thr Ser Arg Pro Lys Leu Asp Gly Arg Glu Lys Pro
1               5                   10                  15

Phe Lys Val Asp Val Ala Thr Ala Gln Ala Gln Ala Arg Lys Ala Gly
            20                  25                  30

Leu Thr